(12) United States Patent
Lee et al.

(10) Patent No.: US 6,197,553 B1
(45) Date of Patent: *Mar. 6, 2001

(54) METHOD FOR LARGE SCALE PLASMID PURIFICATION

(75) Inventors: Ann L Lee; Sangeetha Sagar, both of Lansdale, PA (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/952,428

(22) Filed: Nov. 7, 1997

Related U.S. Application Data

(63) Continuation-in-part of application No. 08/446,118, filed on May 19, 1995, now abandoned, which is a continuation-in-part of application No. 08/275,571, filed on Jul. 15, 1994, now abandoned.

(51) Int. Cl.$^7$ .............................. C12P 19/34; C07H 21/00
(52) U.S. Cl. .................... 435/91.1; 435/320.1; 435/259; 435/306.1; 536/25.4; 536/23.1; 424/184.1; 514/44
(58) Field of Search ............................... 435/91.1, 320.1, 435/259, 306.1; 536/25.4, 23.1; 424/184.1; 514/44

(56) References Cited

U.S. PATENT DOCUMENTS

| | | | |
|---|---|---|---|
| 3,928,642 | * 12/1975 | Hubert et al. | 426/521 |
| 4,830,969 | * 5/1989 | Holmes | 435/259 |
| 5,256,549 | * 10/1993 | Urdea | 435/91 |

FOREIGN PATENT DOCUMENTS

| | | |
|---|---|---|
| WO91/06309 | 5/1991 | (WO) . |
| WO93/24640 | 12/1993 | (WO) . |
| WO95/07995 | 3/1995 | (WO) . |
| WO96/26558 | 2/1996 | (WO) . |
| WO96/36706 | 11/1996 | (WO) . |

OTHER PUBLICATIONS

Ulmer et al, Science 259: 1745–1749 (1993).*
Wang et al, Proc. Nat. Acad. Sci. 90:4156–4160 (1993).*
Robinson t al, Vaccine 11(9):957–960 (1993).*
Holmes et al, Anal. Biochem. 114:193–197 (1981).*
Cohen et al. 'Naked DNA Points Way to VAccines' Science, vol. 259, pp. 1691–1692 (1993).
Wang, 'Simplified Lage–Scale Alkaline Lysis Preparation of Plasmid DNA with Minimal Use of Phenol', Benchmarks, BioTechniques, vol. 17, No. 1 pp. 26–28 (1994).
Montgomery et al. 'Heterologous and Homologous Protection Against Influenza A by DNA Vaccination: Optimization fo DNA Vectors', DNA and Cell Biology, vol. 12, No. 9, pp. 777–783.
LaBrun et al.'Preparation of the Covalently Closed Circular Form of Plasmid DNA', BioTechniques, vol. 6, No. 9, pp. 834–837 (1988).
Sambrook et al. Molecular Cloning—A Laboratory Manual, Cold Spring Harbor Lab. Press, p. 1.34–1.35 (1989).
Hines, et al. 'Large–Scale Purification of Plasmid DNA by Anon–Exchange High Performance Liquid Chromatography', BioTechniques, vol. 12 No. 3, pp. 430–434 (1992).
Colote et al. 'Utilisation de la Chromatographie Liquide a Haute Performance en Genie Genetique', BioSciences, vol. 8, No. 1–2, pp. 42–45 (1989).

* cited by examiner

*Primary Examiner*—Francisco Prats
(74) *Attorney, Agent, or Firm*—J. Mark Hand; Jack L. Tribble

(57) ABSTRACT

A process is disclosed for the large scale isolation and purification of plasmid DNA from large scale microbial fermentations. The process exploits a rapid heating method to induce cell lysis and precipitate genomic DNA, proteins and other debris while keeping the plasmid in solution. Suspending the microbial cells in buffer and then heating the suspension to about 70–100° C. in a flow-through heat exchanger results in excellent lysis. Continuous flow or batch-wise centrifugation of the lysate effects a pellet that contains the cell debris, protein and most of the genomic DNA while the plasmid remains in the supernatant. This invention offers a number of advantages including higher product recovery than by chemical lyses, inactivation of Dnases, operational simplicity and scaleability.

16 Claims, 9 Drawing Sheets

METHOD FOR LARGE SCALE PLASMID PURIFICATION

RELATED APPLICATION

This is a 35 U.S.C. §371 U.S. national application of PCT/US96/07083, filed May 15, 1996, which is a continuation-in-part of U.S. application Ser. No. 08/446,118, filed May 19, 1995, now abandoned, which is a continuation-in-part of U.S. application Ser. No. 08/275,571, filed Jul. 15, 1994, now abandoned.

BACKGROUND OF THE INVENTION

The classical techniques for isolating plasmid DNA from microbial fermentations are suitable for small or laboratory scale plasmid preparations. One such procedure involves the alkaline lysis of microbial host cells containing the plasmid, followed by acetate neutralization causing the precipitation of host cell genomic DNA and proteins which are then removed by, for example, centrifugation. The liquid phase contains the plasmid DNA which is alcohol precipitated and then subjected to isopycnic centrifugation using CsCl in the presence of ethidium bromide. The ethidium bromide is required in order to separate the total plasmid DNA into the three different forms, supercoiled (form I), nicked circle (form II), and linearized (form III), and the desired plasrnid form is collected. Further extraction with butanol is required to remove residual ethidium bromide followed by DNA precipitation using alcohol. Additional purification steps follow to remove host cell proteins. The removal of host proteins is performed by repeated extractions using phenol or a mixture of phenol and chloroform. The plasmid DNA is alcohol precipitated and residual phenol is removed by repeated isoamyl/chloroform extractions. The final alcohol precipitated plasmid DNA is dissolved in water or a suitable buffer solution.

There are numerous drawbacks and limitations to this process including:

a) this process requires the use of expensive and hazardous chemicals (CsCl and EtBr, which are used within the density gradient centrifugation; EtBr is a known mutagen and must be removed from products; also it is an intercalating agent which can nick the plasmid);

b) the density centrifugation step is not easily scaleable;

c) there is a need for organic solvent extraction to remove residual EtBr;

d) phenol extraction is used to remove residual proteins and DNase, a process that would require a centrifuge to break phenol/water emulsion;

e) highly repetitive steps making it laborious and time consuming (isolation requires several days);

f) scalability of the chemical lysis step is an obstacle i.e., lysozyme/alkaline/KOAc treatment step is efficient in lysing cells on a small scale, however, the increase in viscosity makes large scale processing very difficult; and g) use of large quantities of lysozyme to enzymatically weaken the microbial cell wall prior to lysis.

The mixture is then neutralized by addition of acid which results in precipitation of the high molecular weight chromosomal DNA. The high molecular weight RNA and protein-SDS complexes precipitate with the addition of high concentration of KOAc salt. The plasmid product remains in the clarified supernatant following centrifugation. Limitations here include the need to process quickly and on ice in order to retard the activity of nucleases which are not removed until phenol extraction. The main contaminant remaining in the supernatant with the product is RNA.

Another commonly utilized method for isolating and purifying plasmid DNA from bacteria provides a rapid process suitable for only very small scale preparations.

Holmes and Quigley (1981, *Analytical Biochem.*, 114, pp 193–197) reported a simple and rapid method for preparing plasmids where the bacteria are treated with lysozyme, then boiled at about 100° C. in an appropriate buffer (STET) for 20–40 seconds forming an insoluble clot of genomic DNA, protein and debris leaving the plasmid in solution with RNA as the main contaminant. Lysozyme is apparently a requirement for this technique to work, and as such adds a treatment step which is less desirable for large scale manufacture of DNA for human or veterinary use. However, the addition of lysozyme may enhance plasmid release during lysis. An advantage is that heat treatment of the cells would also denature the DNase. However, this technique is not suitable for scale up to a high volume of microbial fermentations and is meant for fermentations less than five liters.

Alternatives to isopycnic centrifugation using CsCl for plasmid purification have been published. These alternatives are suitable only for laboratory scale plasmid isolation and include:

a) size exclusion chromatography, which is inherently limited in throughput;

b) hydroxyapatite chromatography, which has the disadvantage of requiring high concentrations of urea for efficiency;

c) reversed phase chromatography; and d) ion exchange chromatography.

Large scale isolation and purification of plasmid DNA from large volume microbial fermentations, therefore, requires the development of an improved plasmid preparation process. An isolation and purification process for large scale plasmid DNA production is necessitated by recent developments in many areas of molecular biology. In particular, recent advances in the field of polynucleotide-based vaccines for human use, and potentially human gene therapy, requires the ability to produce large quantities of the polynucleotide vaccine in a highly purified form.

Unprecedented technology is required for developing/-implementing a large scale commercially viable process for fermentation, isolation, purification and characterization of DNA as a biopharmaceutical.

SUMMARY OF THE INVENTION

The current laboratory method used to isolate and purify plasmid DNA consists of a series of classical laboratory techniques that are not suitable for a manufacturing process. For example, density gradient centrifugations are not scaleable; the purification procedure necessitates the use of hazardous and expensive chemicals/solvents such as ethydium bromide, a known mutagen, and is labor intensive and time consuming. Therefore, a scaleable alternative process was developed, and is disclosed herein. In addition, an HPLC assay was established to track the plasmid product through the process steps and to distinguish between the plasmid forms. The microbial cells harboring the plasmid are suspended and optionally incubated with lysozyme in a buffer containing detergent, heated using a flow-through heat exchanger to lyse the cells, followed by centrifugation. After centrifugation the clarified lysate, which contains predominately RNA and the plasmid product, is filtered through a 0.45 micron filter and then diafiltered, prior to loading on the anion exchange column. The plasmid product may optionally be treated with RNase before or after filtration, or at an earlier or later step. The anion exchange product fraction containing the plasmid is loaded onto the reversed phase column, and is eluted with an appropriate buffer, providing highly pure plasmid DNA suitable for human use.

DETAILED DESCRIPTION OF THE INVENTION

Figure 1:
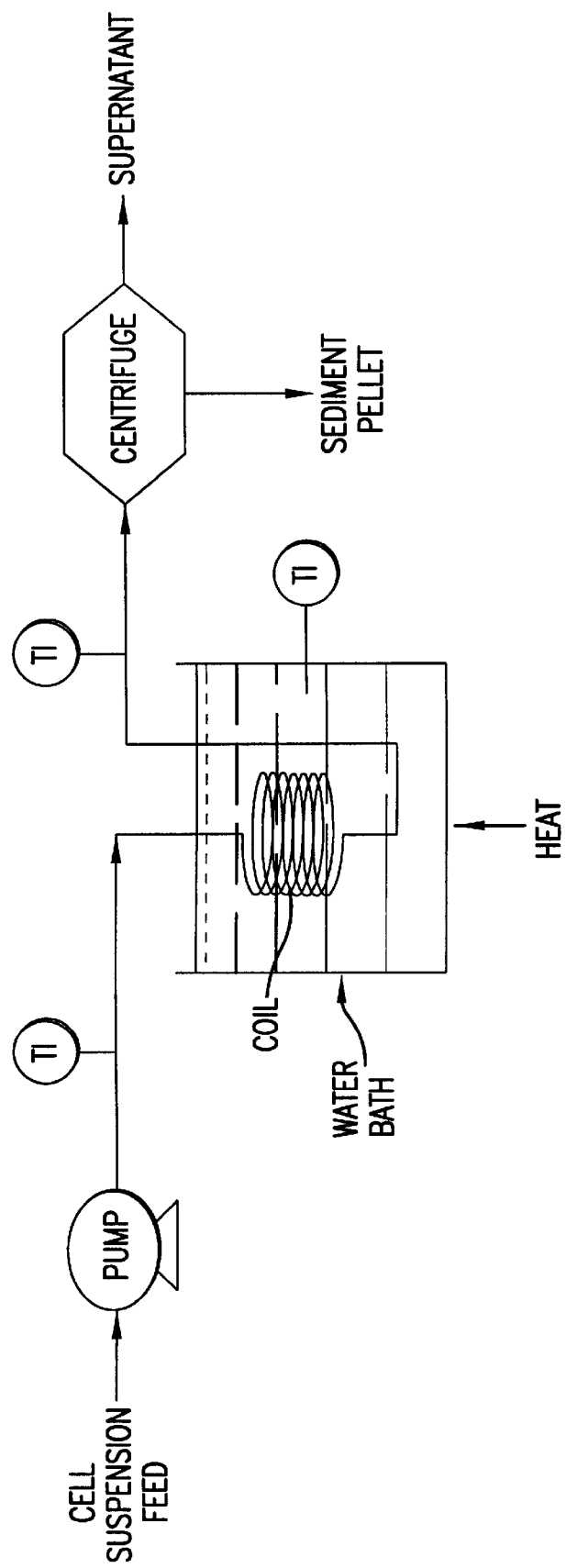
FIG. 1. A schematic of a suitable heat exchanger apparatus is shown.

We have identified a novel, scaleable, alternative lysis/debris removal process for large scale plasmid isolation and purification which exploits a rapid heating method to induce cell lysis and precipitate genomic DNA, proteins and other debris while keeping the plasmid in solution. The utility of this process is the large scale isolation and purification of plasmid DNA. We have found that suspending the microbial cells in modified STET buffer (described below) and then heating the suspension to about 70–100° C. in a flow-through heat exchanger results in excellent lysis. Continuous flow or batch-wise centrifugation of the lysate effects a pellet that contains the cell debris, protein and most of the genomic DNA while the plasmid remains in the supernatant. This invention offers a number of advantages including higher product recovery than by chemical lyses, inactivation of DNases, operational simplicity and scaleability.

The present invention is drawn to a process for the large scale isolation and purification of plasmid DNA from microbial fermentations. Large scale microbial cell fermentations as used herein are considered to be total cell fermentation volumes of greater than about 5 liters, or the cells harvested from a fermentation volume greater than about 5 liters.

The present invention is also drawn to providing plasmid DNA in a highly purified form suitable for human use. DNA for human use includes, but is not limited to, polynucleotide vaccines and DNA for human gene therapy. Polynucleotide vaccines are intended for direct injections into humans [Montgomery, D. L. et al., 1993, *Cell Biol.*, 169, pp. 244–247; Ulmer, J. B. et al., 1993, *Science*, 259, pp. 1745–1749].

The present invention is also drawn to an in-line monitoring process for the tracking of the various forms of plasmid DNA through the isolation and purification steps. The various forms of plasmid DNA referred to above which can be individually isolated by the process of the present invention are form I (supercoiled plasmid), form II (nicked or relaxed plasmid), and form III (linearized plasmid).

The process of the present invention is suitable for use with microbial fermentations in general. It is readily apparent to those skilled in the art that a wide variety of microbial cells are suitable for use in the process of the present invention, including but not limited to, fungal cells including yeast, and bacterial cells. A preferred microbial fermentation is a bacterial fermentation of cells containing the plasmid to be isolated and purified. A preferred bacterial fermentation is a fermentation of *E. coli* containing the plasmid to be isolated and purified. It is readily apparent to those skilled in the art that bacterial fermentations other than *E. coli* fermentations are suitable for use in the present invention. The microbial fermentation may be grown in any liquid medium which is suitable for growth of the bacteria being utilized.

The plasmid to be isolated and purified by the process of the present invention can be any extrachromosomal DNA molecule. The plasmids can be high copy number per cell or low copy number per cell. The plasmids can also be of virtually any size. It is readily apparent to those skilled in the art that virtually any plasmid in the microbial cells can be isolated by the process of the present invention.

Microbial cells containing the plasmid are harvested from the fermentation medium to provide a cell paste, or slurry. Any conventional means to harvest cells from a liquid medium is suitable, including, but not limited to centrifugation or microfiltration.

Isolation of the plasmid DNA from harvested microbial cells using the current lab scale procedures consist mainly of enzymatic treatment of microbial cells to weaken the cell wall followed by cell lysis. The purification steps include repetitive CsCl/EtBr centrifugations followed by organic solvent extractions and precipitation to remove tRNA, residual proteins, EtBr and other host contaminants. These steps are not scaleable and therefore not suitable for use in large-scale processing. In contrast, preparative scale chromatography is a powerful purification tool that provides high resolution, operational ease and increased productivity for purifying DNA plasmid products. Two different modes of chromatography, reversed phase and anion exchange, show suitability in purifying DNA plasmid to the stringent levels required for human use. Separations based on reversed phase are governed by hydrophobic interactions while those for anion exchange are based on electrostatic interaction. These two orthogonal chromatography steps achieve separations between various forms of plasmid (supercoiled, open relaxed, linear and concatemers) and remove host contaminants like LPS (endotoxin), RNA, DNA and residual proteins.

In the process of the present invention, harvested microbial cells are resuspended in modified STET buffer which is comprised of about 50 mM TRIS, about 50–100 mM EDTA, about 8% Sucrose, about 2% TRITON X-100, and optionally sub-microgram concentrations of lysozyme, at a pH in the range of 6.0–10.0. The concentration of lysozyme optionally used in the process of the present invention is substantially less than the concentration of lysozyme used in the procedures known in the art. It is readily apparent to those skilled in the art that modifications of this basic buffer formula can be made and are suitable for use in the present invention. Modifications to this basic buffer formula that do not substantially affect or alter the outcome of the present process are intended to be within the scope of the process of the present invention. The pH range may be adjusted according to the best results provided for the particular strain of bacteria being used. The preferred pH range is about 8.0–8.5. The suspension is then heated to about 70–100° C., with about 70–77° C. preferred, in a flow-through heat exchanger. The lysate is centrifuged to pellet large cell debris, protein and most genomic DNA.

A prototype heat exchanger was built to demonstrate the feasibility of flow-through heat lysis of microbial cells containing plasmid. The particular heat exchanger consisted of a 10 ft.×0.25 inch O.D. stainless steel tube shaped into a coil. The coil was completely immersed into a constant high temperature water bath. The hold-up volume of the coil was about 50 mL. Thermocouples and a thermometer were used to measure the inlet and exit temperatures, and the water bath temperature, respectively. The product stream was pumped into the heating coil using a Masterflex peristaltic pump with silicone tubing. Cell lysate exited the coil and was then centrifuged in a Beckman J-21 batch centrifuge for clarification. FIG. 1 provides a schematic of this particular apparatus, however other types of heat exchanger construction are suitable for use in the present invention, including but not limited to a shell and tube construction, which is preferrable.

After centrifugation, the clarified lysate can optionally be treated with RNase, and the plasmid product can be filtered to further remove small debris. A wide variety of filtration means are suitable for use in this process, including but not limited to filtration through a membrane having a small pore size. A preferred filtration method is filtration through a 0.45 micron filter.

To further remove contaminants from the DNA product, the material can be diafiltered. Standard, commercially available diafiltration materials are suitable for use in this process, according to standard techniques known in the art. A preferred diafiltration method is diafiltration using an ultrafilter membrane having a molecular weight cutoff in the range of 30,000 to 500,000, depending on the plasmid size. The DNA preparation described above is diafiltered using an ultrafiltration membrane (about 100,000 molecular weight cutoff) against column buffer prior to loading on the anion exchange column. Diafiltration prior to the anion exchange column is preferred, and it greatly increases the amount of lysate that can be loaded onto the column.

Figure 5:
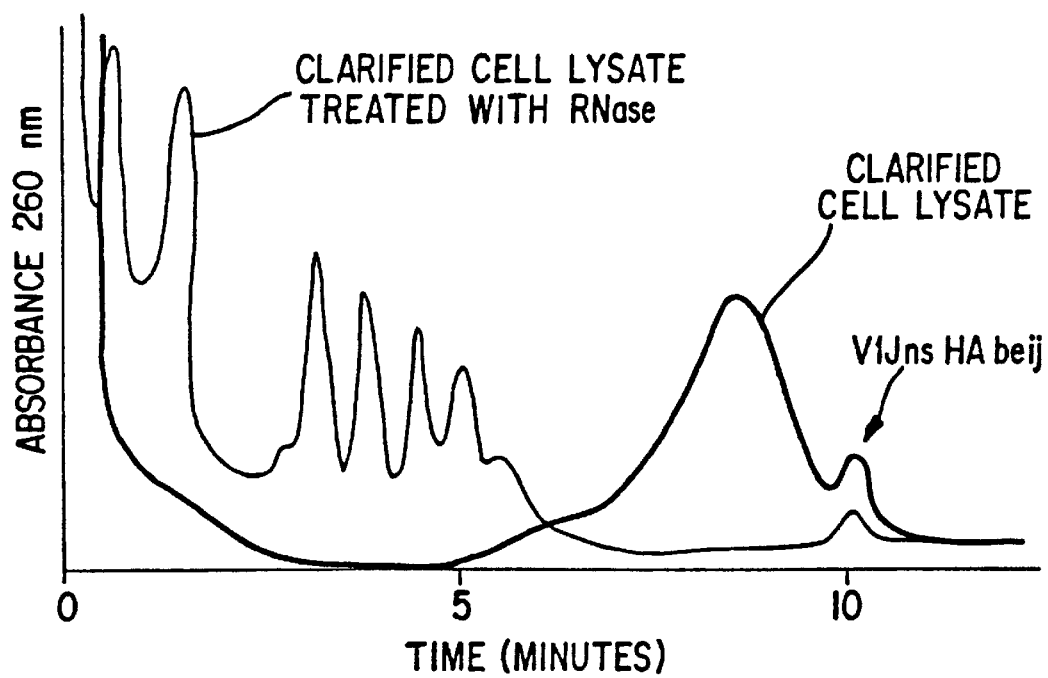
FIG. 5 The elution profiles of anion exchange columns run with RNase treated (bold line) and untreated (thin line) clarified lysates are shown.

A wide variety of commercially available anion exchange matrices are suitable for use in the present invention, including but not limited to those available from POROS Anion Exchange Resins, Qiagen, Toso Haas, Sterogene, Spherodex, Nucleopac, and Pharmacia. The column (Poros II PI/M, 4.5 mm×100) is initially equilibrated with 20 mM Bis/TRIS Propane at pH 7.5 and 0.7 M NaCl. The sample is loaded and washed with the same initial buffer. An elution gradient of 0.5 M to 0.85 M NaCl in about 25 column volumes is then applied and fractions are collected. Anion exchange chromatography is an ideal first polishing step because it provides excellent clearance of RNA, genomic DNA and protein. FIG. 5 (bold) shows a sample elution profile of filtered clarified cell lysate from the anion exchange column. Agarose gel analysis revealed that the second peak which appears after the flow-through is composed of the plasmid product. The earlier large peak is due to RNA. This is confirmed by incubating the clarified cell lysate with ribonuclease prior to loading on the column, which showed that the large peak disappears and is replaced by several smaller more rapidly eluting peaks, due to the degradation products of ribonuclease digestion.

The anion exchange product fraction is loaded onto a reversed phase column. A wide variety of commercially available matrices are suitable for use in the present invention, including but not limited to those available from POROS, Polymer Labs, Toso Haas, Pharmacia, PQ Corp., Zorbax, BioSepra resins, BioSepra Hyper D resins, BioSepra Q-Hyper D resins and Amicon. The matrices can also be polymer based or silica based. The reversed phase column (Poros R/H), is equilibrated with about 100 mM Ammonium Bicarbonate at pH 8.5. A gradient of 0–11% isopropanol is then used to elute bound material. The three forms of plasmids, forms I, II and III described above, can be separated by this method.

The eluted plasmid DNA can then be concentrated and/or diafiltered to reduce the volume or to change the buffer. For DNA intended for human use it may be useful to diafilter the DNA product into a pharmaceutically acceptable carrier or buffer solution. Pharmaceutically acceptable carriers or buffer solutions are known in the art and include those described in a variety of texts such as Remington's Pharmaceutical Sciences. Any method suitable for concentrating a DNA sample is suitable for use in the present invention. Such methods includes diafiltration, alcohol precipitation, lyophilyzation and the like, with diafiltration being preferred. Following diafiltration the final plasmid DNA product may then be sterilized. Any method of sterilization which does not affect the utility of the DNA product is suitable, such as sterilization by passage through a membrane having a sufficiently small pore size, for example 0.2 microns and smaller.

The following examples are provided to illustrate the process of the present invention without, however, limiting the same thereto.

EXAMPLE 1

Growth of Microbial Cells, Cell Lysis and Clarification

One liter of frozen *E. coli* cell slurry was used to make 8 liters of cell suspension in STET buffer (8% sucrose, 0.5% TRITON, 50 mM TRIS buffer, pH 8.5 and 50 mM EDTA). The absorbance of the cell suspension at 600 nm was about O.D. 30. The suspension was stirred continuously to ensure homogeneity. The viscosity of the cell suspension was measured to be about 1.94 cp at room temperature (24° C.). The cell suspension was pumped through the heat exchanger at 81 mL/min which corresponded to a residence time of the cell solution in the heat exchanger of about 35 seconds. The bath temperature was maintained at 92° C. The inlet and outlet temperatures of the cell solution were measured to be about 24° C. and about 89° C. (average), respectively. About 1 liter of sample was run through the heat exchanger. No visible clogging of the tube was observed although the lysate was somewhat thicker than the starting material. The lysate was cooled to room temperature and its viscosity was measured to be about 40 cp. The cell lysate was clarified by batch centrifugation at 9000 RPM for 50 minutes using the Beckman J-21. Analysis of the supernatant confirmed effective cell lysis and product recovery. The product yield produced by flow-through heat lysis was at least comparable to that made by the Quigley & Holmes boiling method. The latter method; however, must be carried out at the laboratory scale in batch mode and is therefore unsuitable for large-scale (5 liters or greater) processing. Since the heat exchanger process is flow-through, there is no maximum limit to the volume of cell suspension that can be processed. This process can therefore accomodate very large scale fermentations of bacteria to produce large quantities of highly purified plasmid DNA.

The clarified lysate was then filtered through a membrane having a pore size of 0.45 microns to remove finer debris. The filtrate was then diafiltered using a membrane having a molecular weight cutoff of about 100.000.

EXAMPLE 2

Control and Reproducibility of Cell Lysis with the Heat Exchanger

Figure 2:
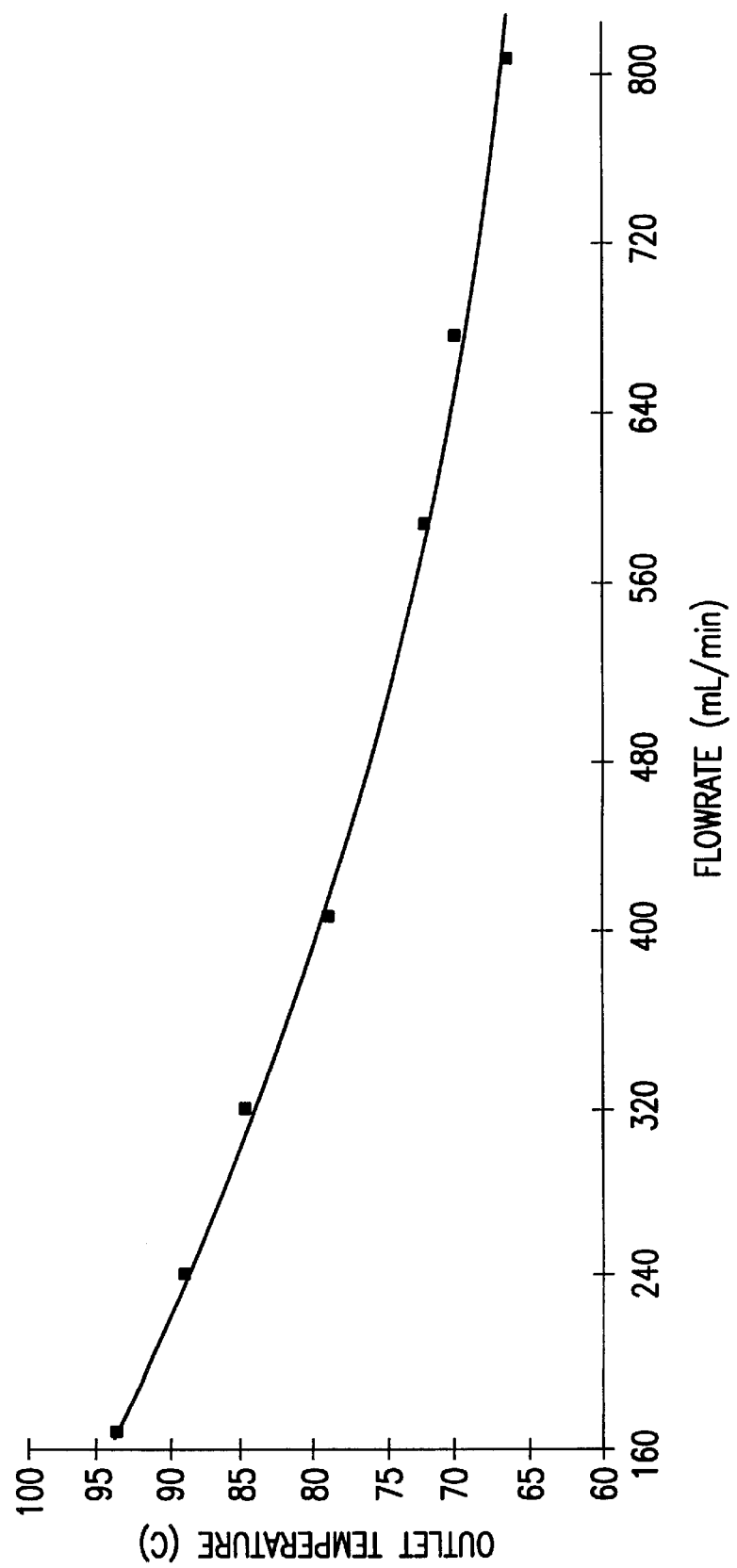
FIG. 2 The relationship between the outlet temperature and the flow rate is shown, graphically.

Adjusting the flowrate (i.e., residence time) at which the cell slurry is pumped through the heat exchanger permits tight control of the temperature of lysis, i.e., the outlet temperature. A cell slurry solution was prepared as described in Example 1 and pumped through the heat exchanger at flow rates ranging from 160 to 850 mL/min. The corresponding outlet temperatures ranged between 93° C. and 65° C., respectively. FIG. 2 illustrates the relationship between flow rate and temperature. The initial temperature of the cell slurry was 24° C. and the bath temperature was kept constant at 96° C. In addition, a number of runs were performed where an outlet temperature of 80° C. was targeted. Yields of 24 mg of circular DNA per L of clarified supernatant were consistently obtained demonstrating the reproducibility of the process.

EXAMPLE 3

Purification of Plasmid DNA

Microbial cells and lysates were prepared as described in Examples 1 and 2, and the following analyses were performned.

Figure 3:
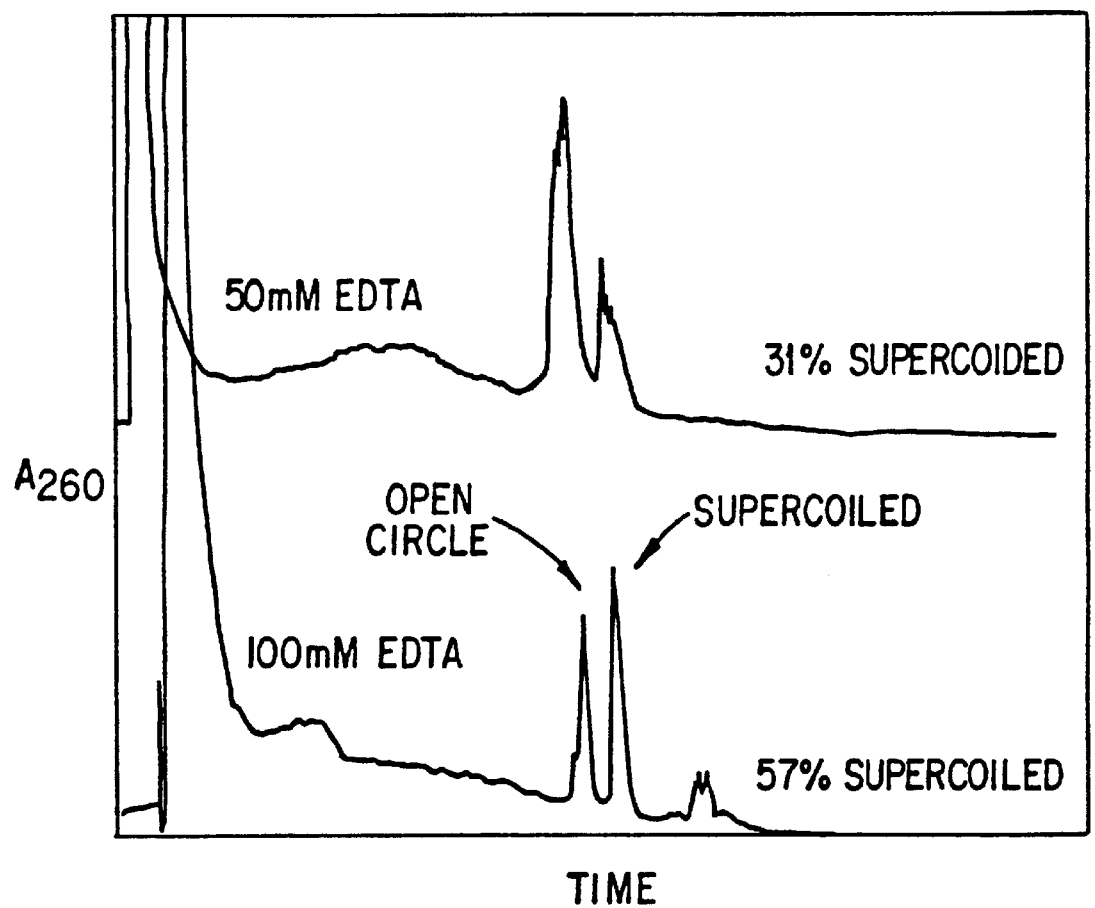
FIG. 3 Comparative chromatograms of total plasmid in clarified supernatant with 50 mMEDTA and 100 mMEDTA are shown.

To illustrate that the addition of 100 mM EDTA vs 50 mM EDTA increased the percentage of supercoiled DNA, and to determine an acceptable range of outlet temperatures (i.e., lysis temperature) with respect to recovery of supercoiled DNA, the following analyses were performed. The supercoiled form of plasmid DNA is desirable since it is more stable than the relaxed circle form. One way that supercoiled DNA can be converted to open circle is by nicking with DNase. We found that the addition of 100 mM EDTA vs 50 mM in the STET buffer minimized the formation of open circle plasmid. FIG. 3 shows comparative chromatograms of the total plasmid in the clarified supernatant with 50 mM EDTA vs 100 mM EDTA. The cell suspension was prepared as described in Example 1. The operating flow rate for these runs was approximately 186 ml/min. The temperatures of the inlet, outlet and bath are 24° C., 92° C. and 96° C. respectively.

Figure 4:
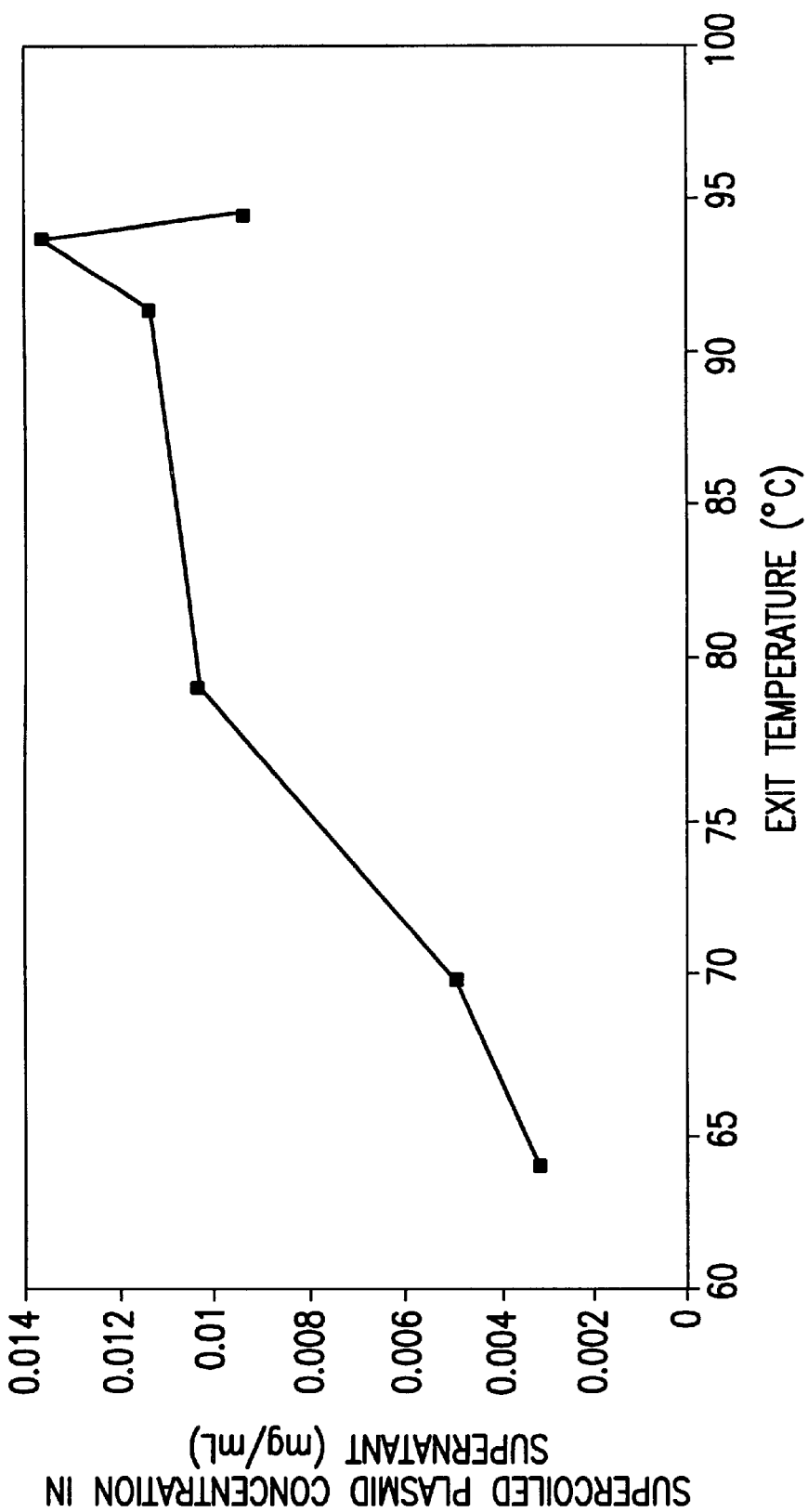
FIG. 4 The yield of supercoiled plasmid as a function of exit temperature is shown.

An acceptable range of lysis temperatures was determined by measuring the percentage of supercoiled plasmid generated for each run. FIG. 4 illustrates the concentration of supercoiled plasmid as a function of exit temperature. An acceptable range of lysis temperatures is between 75° C. and 92° C. At temperatures below 75° C., more relaxed circle plasmid was generated, most likely due to increased DNase activity. Above 93° C., the levels of supercoiled plasmid appear to diminish, possibly due to heat denaturation.

Following continuous heat lysis and centrifugation, 1 mL of clarified lysate was either incubated with 5 μg RNase for 2 hours, or was used untreated. The RNase treated and untreated samples were then loaded onto an anion exchange column (Poros Q/M 4.6×100) that had been previously equilibrated with a 50—50 mixture of solvents A and B [HPLC solvent A: 20 mM Tris/Bis Propane, pH 8.0; and solvent B: 1 M NaCl in 20 mM Tris/Bis Propane, pH 8.0]. The column was eluted using a gradient of 50% to 85% B run over 100 column volumes. Open circle plasmid elutes at approximately 68% B and supercoiled elutes at 72% B.

A comparison of the anion exchange column eluate from clarified lysate treated with RNase (thin line) and untreated (thick line) is shown in FIG. 5. The peak at about 10 minutes is plasmid DNA, and is followed by a large peak in the untreated sample which is RNA. In the RNase treated sample the large RNA peak has been eliminated and a greater separation of the plasmid peak from contaminant peaks is produced.

Figure 6:
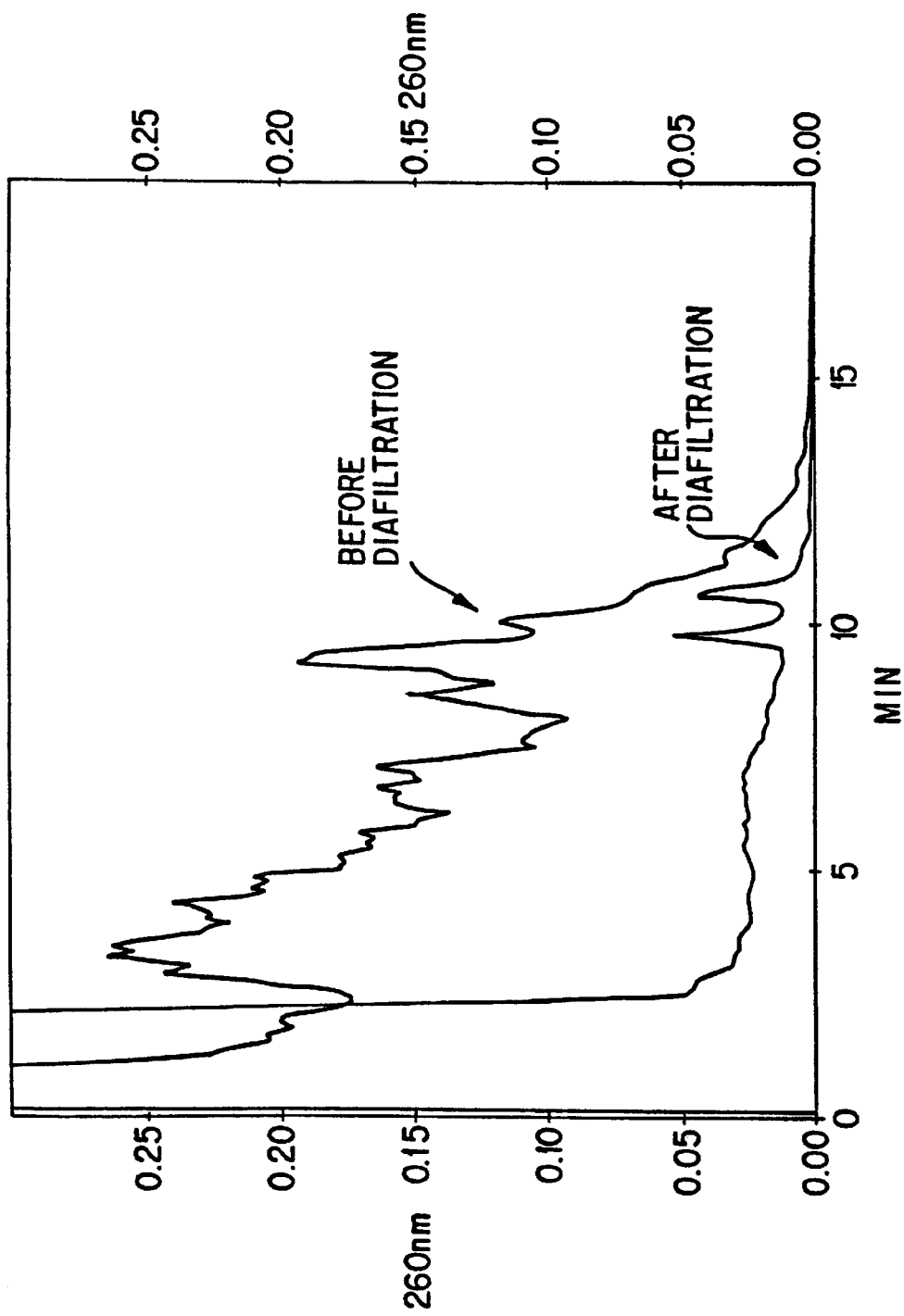
FIG. 6 The elution profiles of anion exchange chromatography with clarified lysate that was diafiltered before the column or not diafiltered before the column are shown.

As described above, diafiltration prior to anion exchange chromatography greatly increases the amount of lysate that can be loaded onto the column. This is demonstrated in FIG. 6 which shows a comparison of clarified lysate which was diafiltered and clarified lysate which was not diafiltered prior to anion exchange chromatography. Samples were prepared as described above except that one sample was diafiltered before loading onto the anion exchange column, and the other sample was not diafiltered. The column was run and eluted as described above. FIG. 6 shows that the amount of contaminant material eluted from the column is vastly greater in the sample that was not diafiltered. The large amount of contaminating material which binds the anion exchange column matrix can overwhelm the maximunm capacity of the column causing loss of DNA product because of the unavailability of the matrix to bind any more material. Therefore, diafiltration removes contaminants and allows more of the DNA product to bind the anion exchange matrix, and in turn allows a greater volume of clarified lysate to be loaded onto the column.

Figure 7:
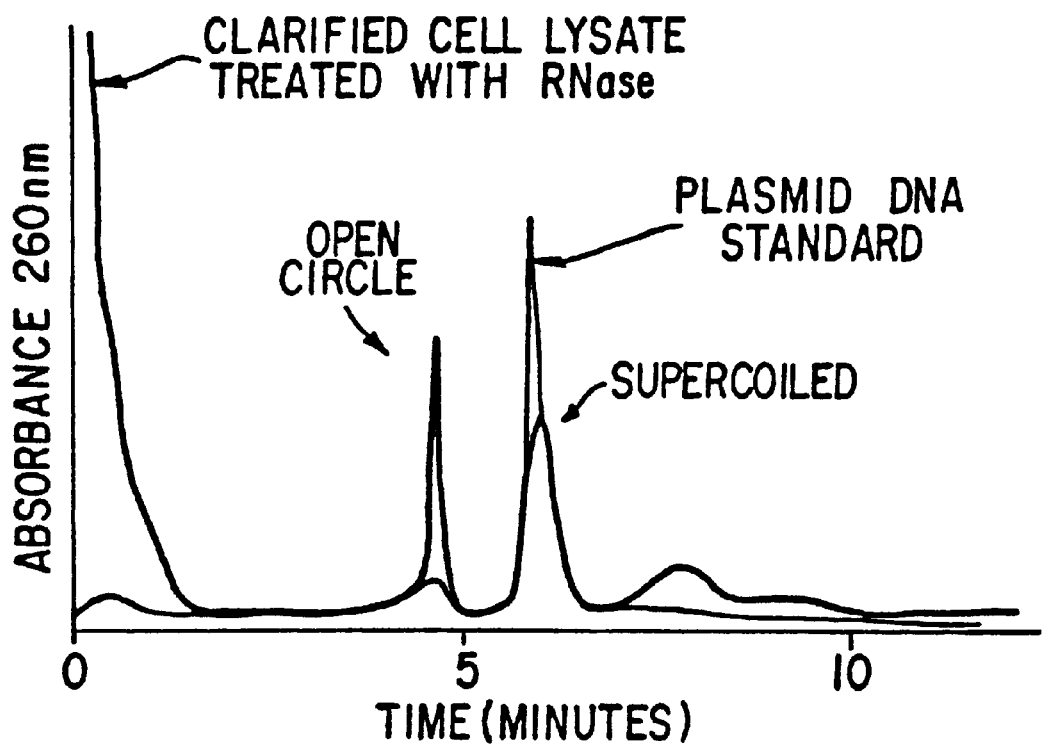
FIG. 7 An elution profile of plasmid DNA from cell lysate is shown.

The plasmid DNA eluted from the anion exchange column was separated into the individual forms by reversed phase HPLC analysis. The separation of supercoiled plasmid (form 1) from nicked circle (form 2) is shown in FIG. 7. The two forms were easily separated and allowed the isolation of individual forms of the plasmid.

EXAMPLE 4

Highly Purified Plasmid DNA From a Chromatoiraphy-based Process

A fermentation cell paste was resuspended in modified STET buffer and then thermally lysed in a batchwise manner. Alternatively a fermentation cell paste is resuspended in modified STET buffer and then thermally lysed in the flow-through process described above. The lysate was centrifuged as described above. Twenty ml of the supernatant were filtered as described above and loaded onto an anion exchange column (Poros Q/M 4.6×100) that was previously equilibrated with a 50—50 mixture of buffers A and B described above. A gradient of 50% to 85% B was run over 50 column volumes with a flow rate of 10 ml/minute. Fractions of 2.5 ml each were collected from the column. The supercoiled plasmid DNA eluted from the column at 72% B.

The anion exchange product was then loaded onto a reversed phase chromatography column (Poros R/H) which had been previously equilibrated with 100 mM ammonium bicarbonate at pH 8.0, and a gradient of 0% to 80% methanol was used to elute the bound material. The highly purified supercoiled plasmid DNA eluted at 22% methanol.

Figure 8:
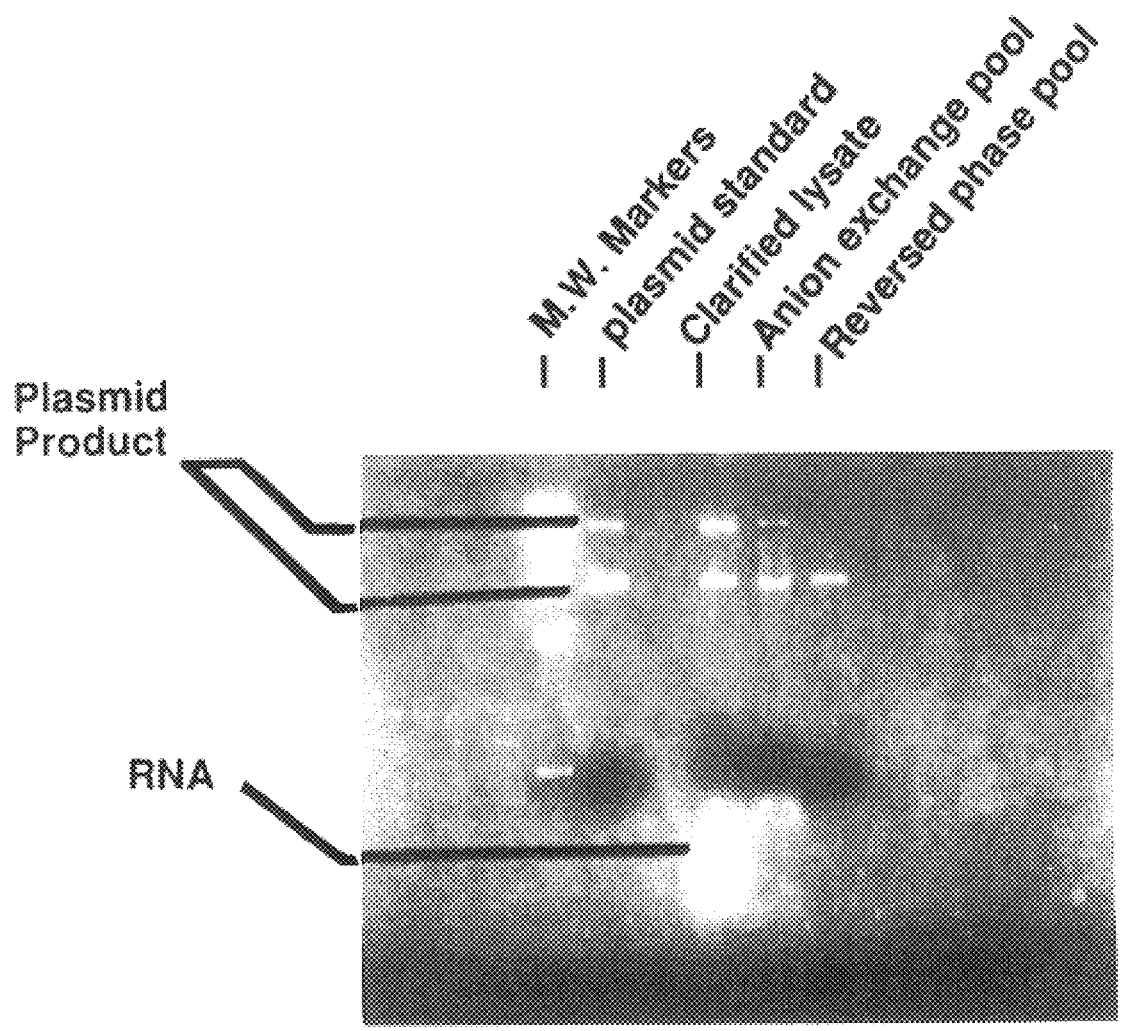
FIG. 8 An agarose gel electrophoresis analysis of the DNA product obtained at various intermediate steps of purification is shown.
Figure 9:
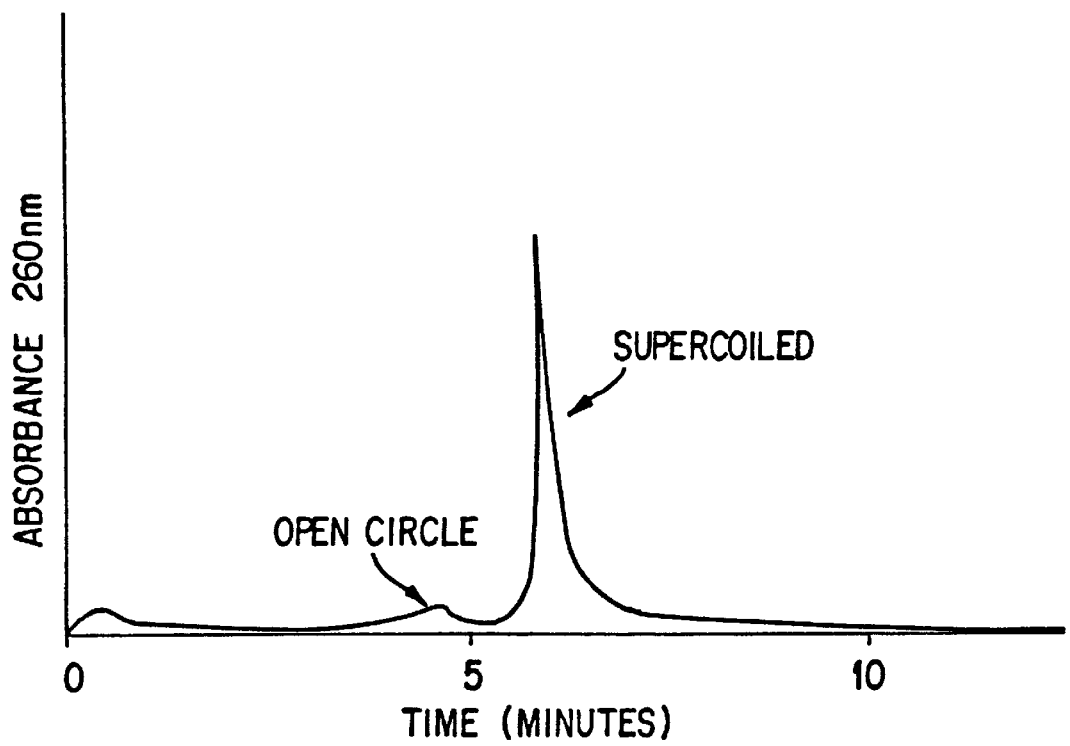
FIG. 9 A tracing of the anion exchange HPLC analysis of the DNA product demonstrating the purity of the product is shown.

An agarose gel of the product fractions from each of the major steps of the purification processis shown in FIG. 8. Based on the agarose gels and the colorimetric and HPLC assays described in Example 3, the final product, shown in FIG. 9, is highly pure. The product consists of greater than 90% supercioled and less than 10% open circle plasmid. RNA was below the limits of detection of the assay used. Genomic DNA and protein contaminant levels were also below the limits of detection in the assays used. The overall supercoiled plasmid yield at the end of the process was approximately 60% of the supercoiled plasmid in the clarified lysate.

EXAMPLE 5

Multi-Gram Scale Purification of Plasmid DNA 4.5 L of frozen $E.\ coli$ cell slurry was used to make 33.7 L of cell suspension in STET buffer (8% sucrose, 2% Triton, 50 mM Tris buffer, 50 mM EDTA, pH 8.5) with 2500 units/ml of lysozyme. The absorbance of the suspension at 600 nm was about O.D. 30. The suspension was stirred at room temperature for 15 minutes to ensure proper mixing and then was incubated for 45 minutes with continuous stirring at 37° C. Following incubation, mixing was continued at room temperature and the cell suspension was pumped through the heat exchanger at a flowrate of 500 ml/min. The batch temperature was maintained at 100° C. and the inlet and outlet temperatures of the cell suspension were measured to be about 24° C. and between 70–77° C., respectively. The cell lysate exiting the heat exchanger was collected in Beckman centrifuge bottles (500 mls each) and the material was centrifuged immediately in Beckman J-21 centrifuges for 50 minutes at 9000 RPM. Following centrifugation, the supernatant was found to contain 4–5 times more plasmid product than in the case without lysozyme incubation. The supernatant product of the centrifugation was immediately diafiltered against 3 volumes of TE buffer (25 mM Tris-EDTA at pH 8.0) and then incubated with $20 \times 10^5$ units of $E.\ coli$ RNase for 2–4 hours at room temperature. After completion of the incubation, the product solution was then diafiltered an additional 6 volumes with TE buffer using a 100 kD MWCO membrane and then filtered through a 0.45 micron filter to remove residual debris. The filtered lysate was diluted to 0.7 M NaCl with a 20 mM Bis/Tris Propane-NaCl buffer at pH 7.5, which prepares the diluted filtrate for loading onto the anion exchange column. The anion exchange column (3.6 L of POROS PI/M) was previously equilibrated with 20 mM Bis/Tfris Propane and 0.7M NaCl. The filtered lysate was loaded to column capacity. In this case 5 grams of supercoiled plasmid was loaded onto the anion exchange column. After loading, the column was washed with 2–4 column volumes of 20 mM Bis/Tris Propane and 0.7 M NaCl. A 10 column volume gradient from 0.7 M NaCl to 2.0 M NaCl in 20 mM Bis/Tris Propane was performed to clear most of the $E.\ coli$ protein. RNA and some endotoxin. The supercoiled plasmid fraction eluted between 1.4 M and 2.0 M NaCl. The supercoiled fraction from the anion exchange column, which contained 4 grams of supercoiled plasmid was then diluted 2–3 times with pyrogen free water, adjusted to 1.2% IPA and pH adjusted to 8.5 with 1 N NaOH. The diluted anion exchange supercoiled fraction was then loaded onto a 7 L reversed phase column (POROS R2/M) which had been previously equilibrated with 100 mM Ammonium Bicarbonate containing 1.2% IPA. In this case, 3.2 grams of supercoiled plasmid were loaded onto the reversed phase column and then the column was washed with 6–10 column volumes of 1.2% IPA in 100 mM Ammonium Bicarbonate. This extensive wash was performed to clear impurities. Next, a gradient of 1.2% IPA to 11.2% EPA in 5 column volumes was performed. The supercoiled plasmid fraction elutes at about 4% IPA. The supercoiled product fraction from the reversed phase column was then concentrated and diafiltered into normal saline using a 30 kD MWCO membrane. The final product bulk was filtered through a 0.22 micron filter. Table 1 provides a purification table describing clearance of impurities and yields across each of the major process steps. The overall product yield of the process was more than 50% of the supercoiled plasmid in the clarified cell lysate as indicated by the anion exchange HPLC assay described in EXAMPLE 3. The purity of the product was very high with less than 1% $E.\ coli$ RNA and protein, and less than 2.9% $E.\ coli$ genomic DNA.

TABLE 1

MULTI-GRAM PURIFICATION AND RECOVERY SUMMARY

| STEP | Plasmid Product (mg) | % Step Yield | genomic DNA (mg/mg) | Protein (mg/mg) | RNA (mg/mg) | LAL Eu/mg |
|---|---|---|---|---|---|---|
| clarified lysate | 6750 | 100 | 0.52 | 7.6 | 196 | $1.1 \times 10^7$ |
| concentration/RNase/ diafiltration/dead-end filtration | 6500 | 93 | 0.50 | 1.6 | 2.21 | $3.4 \times 10^6$ |
| anion exchange | 4000 of 5000 | 80 | 0.41 | 0.3 | 0.1 | $1.2 \times 10^4$ |
| reversed phase | 2300 of 3200 | 77 | 0.029 | <0.01‡ | <0.01‡ | 62 |
| concentration diafiltration into final buffer | 2110 | 100 | 0.029 | <0.01‡ | <0.01‡ | 2.8 |
| final process yield | | 54 | | | | |

‡below detection limits of assay method

What is claimed is:

1. A process for isolation and purification of plasmid DNA from a large scale microbial cell fermentation with a volume of greater than about 5 liters, comprising:
   a) harvesting the cells;
   b) adding a lysis solution to the harvested cells, resulting in a cell slurry;
   c) heating the cell slurry of step b) in a flow-through heat exchange apparatus wherein the flow rate of the cell slurry through the heat exchange apparatus is adjusted such that the temperature of the cell slurry upon exiting the heat exchange apparatus is from about 70° C. to about 80° C. so as to denature cellular proteins, such that a crude lysate is formed;

d) centrifuging the crude lysite to yield a pellet and a supernatant;

e) filtering and diafiltering the supernatant of step d) to provide a filtrate containing the plasmid DNA;

f) contacting the filtrate of step e) with an anion exchange matrix;

g) eluting and collecting the plasmid DNA from the anion exchange matrix;

h) contacting the plasmid DNA from step g) with a reversed phase high performance liquid chromatography matrix;

i) eluting and collecting the plasmid DNA from the reversed phase high performance liquid chromatography matrix of step h);

j) optionally concentrating and/or diafiltering the product of step i) into a pharmaceutically acceptable carrier;

k) optionally sterilizing the DNA product;

wherein:

the lysis solution of step b) is modified STET buffer and lysozyme, the modified STET buffer consisting essentially of about 50 mM TRIS, about 50–100 mM EDTA, about 8% (w/v) sucrose and about 2% Triton X-100.

2. The process of claim 1 including addition of RNase at any step following step a).

3. A process for preparing a crude lysate from a large scale microbial cell fermentation with a volume of greater than about 5 liters or from microbial cells harvested from such a microbial cell fermentation and resuspended in an appropriate buffer which comprises passing the microbial cells through a flow-through heat exchange apparatus wherein the flow rate of the cells passing through the heat exchange apparatus is adjusted such that the temperature of the cells upon exiting the heat exchange apparatus is from about 65° C. to about 93° C., forming the crude lysate which is amenable to purification and isolation of plasmid DNA contained within the crude lysate.

4. The process of claim 3 wherein the temperature of the cells upon exiting the heat exchanger is from about 70° C. to about 80 C.

5. A process lor preparing a crude lysate from a large scale microbial cell fermentation with a volume of greater than about 5 liters or from microbial cells harvested from such a microbial cell fermentation and resuspended in an appropriate buffer containing a lysis component which comprises passing microbial cells containing the lysis solution through a flow-through heat exchange apparatus wherein the flow rate of the cells passing through the heat exchange apparatus is adjusted such that the temperature of the cells upon exiting the heat exchange apparatus is from about 65° C. to about 93° C., forming the crude lysate which is amenable to purification and isolation of plasmid DNA contained within the crude lysate.

6. The process of claim 5 wherein the temperature of the cells upon exiting the heat exchanger is from about 70° C. to about 80° C.

7. The process of claim 5 wherein the lysis component is lysozyme.

8. The process of claim 6 wherein the lysis component is lysozyme.

9. A process for isolation and purification of plasmid DNA from large scale microbial cell fermentations with a volume of greater than about 5 liters, comprising:

a) harvesting the cells;

b) adding a lysis solution to the harvested cells, resulting in a cell slurry;

c) heating the cell slurry of step b) in a flow-through heat exchange apparatus wherein the flow rate of the cell slurry through the heat exchange apparatus is adjusted such that the temperature of the cell slurry upon exiting the heat exchange apparatus is from about 65° C. to about 95° C. so as to denature cellular proteins, such that a crude lysate is formed;

d) centrifuging the crude lysate to yield a pellet and a supernatant;

e) filtering and diafiltering the supernatant of step d) to provide a filtrate containing the plasmid DNA;

f) contacting the filtrate of step e) with an anion exchange matrix;

g) eluting and collecting the plasmid DNA from the anion exchange matrix;

h) contacting the plasmid DNA from step g) with a reversed phase high performance liquid chromatography matrix;

i) eluting and collecting the plasmid DNA from the reversed phase high performance liquid chromatography matrix of step h);

j) optionally concentrating and/or diafiltering the product of step i) into a pharmaceutically acceptable carrier; and k) optionally sterilizing the DNA product.

10. The method of claim 9 wherein the lysis solution of step b) contains lysozyme.

11. The method of claim 10 wherein the lysis solution of step b) further comprises a modified STET buffer consisting essentially of about 50 mM TRIS, about 50–100 mM EDTA, about 8% (w/v) sucrose and about 2% Triton X-100.

12. The process of claim 11 including addition of RNase at any step following step a).

13. The process of claim 9 wherein the temperature of the cell slurry upon exiting the heat exchanger is from about 70° C. to about 80° C.

14. The method of claim 13 wherein the lysis solution of step b) contains lysozyme.

15. The method of claim 14 wherein the lysis solution of step b) further comprises a modified STET buffer consisting essentially of about 50 mM TRIS, about 50–100 mM EDTA, about 8% (w/v) sucrose and about 2% Triton X-100.

16. The process of claim 15 including addition of RNase at any step following step a).

* * * * *